United States Patent [19]

Aumueller et al.

[11] Patent Number: 4,980,476
[45] Date of Patent: Dec. 25, 1990

[54] POLYALKYLPIPERIDINE-SUBSTITUTED LACTAMS AND USE THEREOF AS STABILIZERS FOR PLASTICS

[75] Inventors: Alexander Aumueller, Deidesheim; Peter Neumann, Mannheim; Hubert Trauth, Dudenhofen, all of Fed. Rep. of Germany

[73] Assignee: BASF Aktiengesellschaft, Ludwigshafen, Fed. Rep. of Germany

[21] Appl. No.: 438,795

[22] Filed: Nov. 20, 1989

[30] Foreign Application Priority Data

Dec. 16, 1988 [DE] Fed. Rep. of Germany ....... 3842304

[51] Int. Cl.$^5$ ............................................. C07D 401/14
[52] U.S. Cl. ...................................... 546/187; 546/190
[58] Field of Search ................................. 546/187, 190

[56] References Cited

U.S. PATENT DOCUMENTS

| 3,684,765 | 8/1972 | Matsui et al. | 260/45.8 N |
|---|---|---|---|
| 4,238,613 | 12/1980 | Rasberger et al. | 546/190 |
| 4,279,804 | 7/1981 | Cantatore et al. | 546/189 |
| 4,762,872 | 8/1988 | Lai et al. | 546/190 |
| 4,769,457 | 9/1988 | Helwig et al. | 544/180 |

*Primary Examiner*—Richard L. Raymond
*Assistant Examiner*—Ba K. Trinh
*Attorney, Agent, or Firm*—Oblon, Spivak, McClelland, Maier & Neustadt

[57] ABSTRACT

Compound of the formula (I)

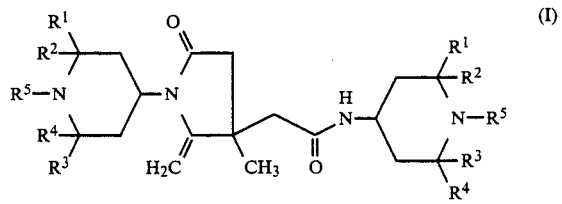

where $R^1$, $R^2$, $R^3$ and $R^4$ are each alkyl or $R^1$ and $R^2$ or $R^3$ and $R^4$ are together tetra- or pentamethylene and $R^5$ is hydrogen, alkanoyl, alkyl, cyanoalkyl, hydroxyalkyl, aminoalkyl or phenylalkyl, in which the phenyl nucleus may be substituted by $C_1$–$C_4$-alkyl, $C_1$–$C_4$-alkoxy or halogen, and the acid addition salts and hydrates of these compounds are useful stabilizers for organic materials, in particular plastics.

4 Claims, No Drawings

POLYALKYLPIPERIDINE-SUBSTITUTED LACTAMS AND USE THEREOF AS STABILIZERS FOR PLASTICS

It is known that polyalkylpiperidine derivatives protect organic polymers from destruction by light and heat.

Unsatisfactory aspects of prior art stabilizers are frequently their incompatibility with polyolefins and other plastics, the short duration of the protective effect, the self-color of the substances and their volatility and thermal decomposition when incorporated into polymers at elevated temperature.

It is an object of the present invention to provide new stabilizers which are free of the above disadvantages.

We have found that this object is achieved by the novel lactams of the formula (I).

The present invention accordingly provides polyalkylpiperidine-substituted lactams of the general formula (I)

where
$R^1$, $R^2$, $R^3$ and $R^4$ are each $C_1-C_4$-alkyl, or $R^1$ and $R^2$ or $R^3$ and $R^4$ are together tetra- or pentamethylene, and $R^5$ is hydrogen, $C_1-C_8$-alkanoyl, $C_1-C_3$-cyanoalkyl, $C_2-C_4$-hydroxyalkyl, $C_2-C_3$-aminoalkyl or $C_7-C_{10}$-phenylalkyl in which the phenyl is unsubstituted or monosubstituted or disubstituted by $C_1-C_4$-alkyl, $C_1-C_4$-alkoxy or halogen, and the acid addition salts and hydrates thereof.

Compounds (I) are very highly suitable for stabilizing organic material, specifically plastics, against degradation by light and heat. They are also effective as metal deactivators. The novel compounds are preferably used for stabilizing polyolefins, in particular polyethylene and polypropylene, and also polyurethanes and ABS.

Compounds (I) are added to the plastics to be stabilized in a concentration of 0.01 to 5% by weight, preferably from 0.02 to 2% by weight, based on the polymer before, during or after polymer formation.

The alkyl $R^1-R^4$ is for example methyl, ethyl, n-propyl, isopropyl, n-butyl or isobutyl. Two adjacent radicals $R^1$ and $R^2$ or $R^3$ and $R^4$ may also be combined to form a tetra- or pentamethylene group.

Preferably, $R^1$, $R^2$, $R^3$ and $R^4$ are each methyl.

Alkyl $R^5$ can be linear or branched. Specific examples are: methyl, ethyl, propyl, n-butyl, n-pentyl, isopentyl, n-hexyl, n-heptyl and n-octyl. Preferred alkyl $R^5$ is methyl.

Alkanoyl $R^5$ is for example propionyl, butanoyl, pentanoyl, hexanoyl, heptanoyl, octanoyl, benzoyl or in particular acetyl. Phenylalkyl $R^5$ is for example phenylethyl or preferably benzyl.

Suitable phenylalkyl with substitution in the phenyl nucleus is for example 3- or 4-methoxybenzyl, 3- or 4-methoxyphenylethyl, 3- or 4-chlorobenzyl, 3- or 4-chlorophenylethyl, 3- or 4-ethoxybenzyl, 3- or 4-ethoxyphenylethyl or preferably 3- or 4-methylbenzyl.

Cyanoakyl $R^5$ is for example cyanoethyl or preferably cyanomethyl.

Hydroxyalkyl $R^5$ is for example 3-hydroxypropyl, 4-hydroxybutyl or preferably 2-hydroxyethyl. Aminoalkyl $R^5$ is for example 3-aminopropyl or preferably 2-aminoethyl. Particularly preferred $R^5$ is hydrogen.

The compounds according to the present invention can be prepared by aminolysis of the compound of the formula (II) with amines of the general formula (III) with or without solvent in the presence of absence of a catalyst. Preferably, an excess of amine is used without solvent and without catalyst at an elevated temperature of from 100° to 220° C., preferably from 110° to 160° C.

Compounds of the general formula (I) where $R^5$ is hydrogen can be converted by art recognized techniques such as alkylation, acylation, Michael addition, cyanomethylation or hydroxyalkylation into compounds of the general formula (I) where $R^5$ is not hydrogen.

The compounds of the formula (I) according to the present invention can be present in the form of the free bases, as hydrates or as salts. Suitable anions are derived for example from inorganic acids, carboxylic acids or sulfonic acids. Of the salts, those of carboxylic and sulfonic acids are preferred.

Suitable inorganic anions are for example chloride, bromide, sulfate, methosulfate, tetrafluoborate, phosphate and thiocyanate.

Carboxylic acid anions are for example: formate, acetate, propionate, hexanoate, cyclohexanoate, lactate, stearate, palmitate, dodecylbenzoate, benzoate, acrylate, methacrylate, citrate, malonate, succinate and anions of polycarboxylic acids such as polyacrylic acid, polymethacrylic acid and (meth)acrylic acid copolymers having up to 3000 COOH groups.

Sulfonic acid anions are for example benzenesulfonate, tosylate and methanesulfonate.

The present invention also relates to the use of (I) as stabilizer for organic material.

Compounds (I) can be incorporated into the plastics to be stabilized in any known apparatus by any known method for incorporating stabilizers or other additives into polymers.

Besides compounds (I) according to the present invention, stabilized plastics may also contain further additives, for example antioxidants, additional light stabilizers, metal deactivators, antistats, flame retardants and also pigments and fillers.

Antioxidants and light stabilizers which may be added to the plastics as well as the compounds according to the present invention are for example compounds based on sterically hindered phenols or sulfur- and/or phosphorus-containing costabilizers.

Such phenolic antioxidants are for example 2,6-di-tert-butyl-4-methylphenol,n-octadecyl β-(3,5-di-tert-butyl-4-hydroxyphenyl)propionate, 1,1,3-tris(2-methyl-4-hydroxy-5-tert-butylphenyl)butane, 1,3,5-trimethyl- 2,4,6-tris(3,5-di-tert-butyl-4-hydroxybenzyl)benzene, 1,3,5-tris(3,5-di-tert-butyl-4-hydroxybenzyl) isocyanurate, 1,3,5-tris[β(3,5-di-tert-butyl-4-hydroxyphenyl)propionyloxyethyl]isocyanurate, 1,3,5-tris(2,6-dimethyl-3-hydroxy-4-tert-butylbenzyl) isocyanurate and pentaerythritol tetrakis[β(3,5-di-tert-butyl-4-hydroxyphenyl)propionate].

Suitable phosphorus-containing antioxidants are for example tris(nonylphenyl) phosphite, distearyl pentaerythritol diphosphite, tris(2,4-di-tert-butylphenyl) phosphite, tris(2-tert-butyl-4-methylphenyl) phosphite, bis(2,4-di-tert-butylphenyl) pentaerythritol diphosphite and tetrakis(2,4-di-tert-butylphenyl)-4,4'-biphenylene diphosphite.

Further antioxidants and light stabilizers which may be used together with the compounds according to the present invention are for example 2-(2'-hydroxyphenyl)benzotriazole, 2-hydroxybenzophenones, phenyl esters of hydroxybenzoic acids, α-cyanocinnamic acid derivatives, nickel compounds, benzimidazolecarboxanilides and/or oxalodianilides.

Suitable organic polymers for stabilization by the compounds according to the present invention are for example:

polymers of mono- and diolefins, such as low and high density polyethylene, linear low density polyethylene, polypropylene, polyisobutylene, poly-1-butene, polyisoprene, polybutadiene and copolymers of mono- or diolefins and mixtures thereof;

copolymers of mono- or diolefins with other vinyl monomers, eg. ethylene/alkyl acrylate copolymers, ethylene/alkyl methacrylate copolymers, ethylene/vinyl acetate copolymers or ethylene/acrylic acid copolymers;

polystyrene;

copolymers of styrene or α-methylstyrene with dienes or acryloyl derivatives, such as styrene/butadiene, styrene-acrylonitrile, styrene/ethyl methacrylate, styrene/butadiene/ethyl acrylate; styrene-acrylonitrilemethacrylate;

ABS, MBS or similar polymers;

halogen-containing polymers, eg. polyvinyl chloride, polyvinyl fluoride, polyvinylidene fluoride and copolymers thereof;

polymers derived from α,β-unsaturated acids and derivatives thereof, such as polyacrylates and polymethacrylates, polyacrylamides and polyacrylonitriles;

polymers derived from unsaturated alcohols and amines and acryloyl derivatives or acetals thereof, such as polyvinyl alcohol or polyvinyl acetate; and polyurethanes, polyamides, polyureas, polyesters, polycarbonates, polysulfones, polyether sulfones and polyether ketones.

Compounds (I) can also be used for stabilizing surface coatings, for example industrial coatings. These include in particular baking finish coatings, among which in turn the automotive coatings, in particular the two-layer coatings, are particularly noteworthy. Here, too, the abovementioned further antioxidants and light stabilizers may also be added.

The compounds according to the present invention can be added to the coating composition in a solid or dissolved form. Here the ready solubility of (I) in coating systems is of particular advantage.

The compounds according to the present invention are suitable in particular for stabilizing polyolefins, in particular ethylene and propylene polymers, polyurethanes, and coating compositions.

PREPARATION EXAMPLE 14.5 g of 1,5-dimethyl-2,8-dioxacisbicyclo-[3.3.0]octa-3,7-dione (preparation see Chem. Ber. 108 (1975), 3256) were heated in 60 g of 4-amino-2,2,6,6-tetramethylpiperidine at 120° C. for 14 hours and then at 150° C. for 10 hours. After cooling down, 250 ml of diethyl ether were added, and the precipitated product was filtered off with suction, washed with diethyl ether and petroleum ether and dried. Yield: 24.0 g of the compound of the formula

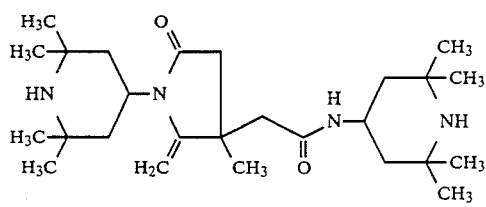

as a colorless solid of melting point 257° C.

| | | | | |
|---|---|---|---|---|
| Calc.: | C 69.6 | H 10.8 | N 12.5 | O 7.1% |
| Found: | C 69.7 | H 10.4 | N 12.5 | O 7.3% |

APPLICATION EXAMPLE

Stabilization of polypropylene (a) 0.25 part of the compound of the Preparation Example is incorporated in 100 parts of polypropylene (1320 H from BASF) by double extruding at 220° C., and the second time the extrudate is pressed in 200 μm thick sheets. After storage in the dark at 25° C. for 14 days the surface of the sheet is free of any coating.

(b) The sheets produced according to a) are tested for weatherability in a Xenotest 1200 accelerated weathering tester. Aging is determined by measuring the CO number at certain intervals. The onset of embrittlement is determined mechanically. The test results are summarized in the table.

TABLE

CO numbers on irradiation in a Xenotest 1200 accelerated weathering tester (polypropylene)

| Added compound | Irradiation time in (h) | | |
|---|---|---|---|
| | 2000 | 3000 | 4000 |
| 1. Preparation example | 9.5 | 18.0 | 22.0 |
| 2. None | brittle | | |

We claim:

1. A polyalkylpiperidine-substituted lactam of the general formula (I)

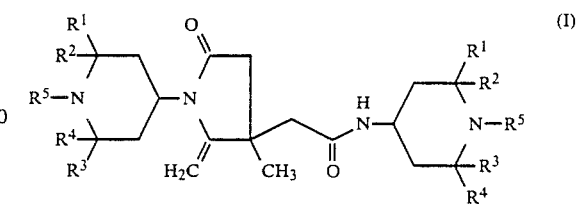

where $R^1$, $R^2$, $R^3$ and $R^4$ are each $C_1$-$C_4$-alkyl, or $R^1$ and $R^2$ or $R^3$ and $R^4$ are together tetra- or pentamethylene, and $R^5$ is hydrogen, $C_1$-$C_8$-alkanoyl, $C_1$-$C_8$-alkyl, $C_1$–$C_3$-cyanoalkyl, $C_2$–$C_4$-hydroxyalkyl, $C_2$–$C_3$-aminoalkyl or $C_7$–$C_{10}$-phenylalkyl in which the phenyl is unsubstituted or monosubstituted or disubstituted by $C_1$–$C_4$-alkyl, $C_1$–$C_4$-alkoxy or halogen, or an acid addition salt or hydrate thereof.

2. A lactam as claimed in claim 1, wherein $R^1$, $R^2$, $R^3$ and $R^4$ are each methyl.

3. A lactam as claimed in claim 1, wherein $R^5$ is hydrogen.

4. A lactam as claimed in claim 2, wherein $R^5$ is hydrogen.

* * * * *